United States Patent [19]
Weber

[11] Patent Number: 5,077,980
[45] Date of Patent: Jan. 7, 1992

[54] CRYOTHERAPY UNIT

[76] Inventor: Dieter Weber, Auf der Tödtheide 19, D-4800 Bielefeld 16, Fed. Rep. of Germany

[21] Appl. No.: 534,515

[22] Filed: Jun. 6, 1990

Related U.S. Application Data

[63] Continuation of PCT/DE88/00561, Sep. 10, 1988

[30] Foreign Application Priority Data

Oct. 15, 1987 [Fed Rep. of Germany] ...... 8713858

[51] Int. Cl.$^5$ .................................................. A61F 7/00
[52] U.S. Cl. ...................................... 62/130; 62/259.3; 128/400; 128/DIG. 27
[58] Field of Search ............... 62/237, 259.3, 293, 62/426; 128/400, DIG. 27

[56] References Cited

U.S. PATENT DOCUMENTS 1,503,528  8/1924  Fabret ............................. 128/400
4,784,140  11/1988  Donnerback et al. ...... 128/DIG. 27

FOREIGN PATENT DOCUMENTS 3414094  10/1984  Fed. Rep. of Germany ...... 128/400
3505044  8/1986  Fed. Rep. of Germany ...... 128/400
508146  4/1955  Italy ................................ 128/400

OTHER PUBLICATIONS

Computer Control of Industrial Processes; Savas, 1965.

*Primary Examiner*—William E. Wayner
*Attorney, Agent, or Firm*—Herbert L. Lerner; Laurence A. Greenberg

[57] ABSTRACT

A cryotherapy unit includes a cooling system to be connected to a current source, an air inlet in communication with the cooling system, and an air outlet in communication with the cooling system.

15 Claims, 1 Drawing Sheet

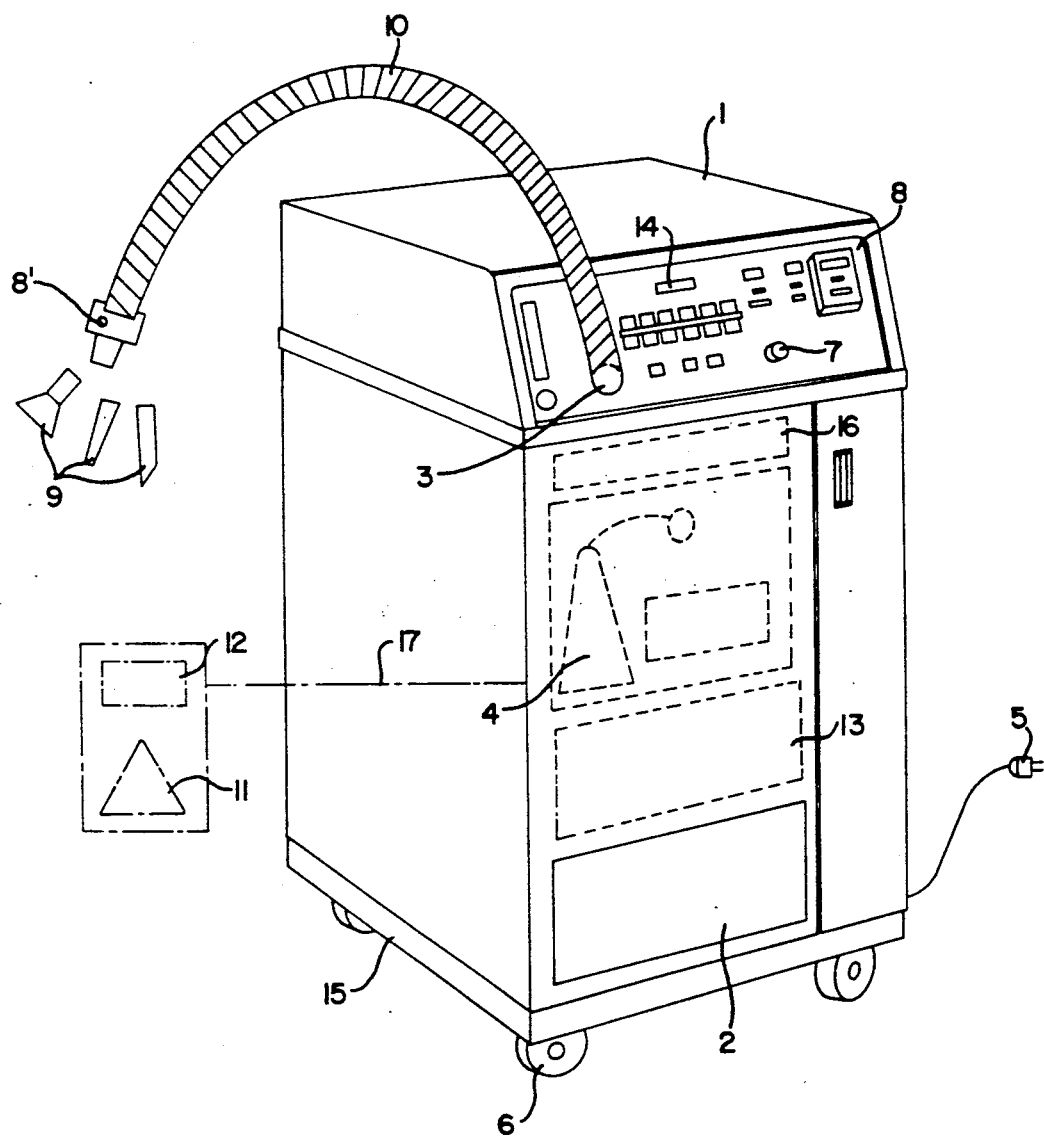

CRYOTHERAPY UNIT

CROSS-REFERENCE TO RELATED APPLICATIONS

This application is a continuation of International Patent Application PCT/DE88/00561, filed Sept. 10, 1988.

The invention relates to a cryotherapy unit, or a therapy unit for cold application.

The therapeutic principle of using cold in various forms for reducing pain and tissue swelling has long been known. The cold can be applied by solid, liquid or gaseous media.

In a gaseous application, the use of nitrogen gases at temperatures of approximately $-196$ C. in physical therapy has been proved to reduce pain in various rheumatic diseases and (contused) injuries in sports medicine. The advantage of the "gassing" procedure with a nitrogen mixture is the extremely low temperature that can be attained in minimal time, even in relatively deep tissues or joint regions.

One of the disadvantages of the nitrogen gassing method is that refilling of the container with liquid nitrogen must be performed very often and is also very expensive.

It is accordingly an object of the invention to provide a cryotherapy unit, which overcomes the hereinaforementioned disadvantages of the heretofore-known devices of this general type and to do so in such a way as to enable its use as prescribed without using liquid nitrogen and while substantially lowering the maintenance costs.

With the foregoing and other objects in view there is provided, in accordance with the invention, a cryotherapy unit, comprising a cooling system, means for connecting said cooling system to a current source, an air inlet in communication with said cooling system, and an air outlet in communication with said cooling system.

In accordance with another feature of the invention, there is provided a therapy unit housing into which said cooling system is integrated.

In accordance with a further feature of the invention, the cooling system is a split system. In accordance with an added feature of the invention, the cooling system has a cooling unit and a condenser disposed outside said therapy unit housing.

With split disposition of the cooling system, it becomes possible to connect other therapy units to one cooling system.

In accordance with an additional feature of the invention, there is provided an isolating hose connected to said air outlet.

In accordance with yet another feature of the invention, there are provided various kinds of slip-on nozzle interchangeably disposed on the free end of said isolating hose.

In accordance with yet a further feature of the invention, there is provided a thermostat control system disposed on said therapy unit housing, in order to set the desired temperature.

In accordance with yet an added feature of the invention, there is provided an acoustic and/or optical signal transducer associated with said air outlet for displaying a deviation of a set temperature for cold air flowing out of said air outlet.

In accordance with yet an additional feature of the invention, there is provided at least one thermometer disposed on said therapy unit housing for measuring the temperature of the ambient air and/or on said isolating hose for measuring the temperature at an application site.

In accordance with again another feature of the invention, there are provided wheels directly or indirectly associated with said therapy unit housing for transportation.

In accordance with again a further feature of the invention, the connecting means are in the form of a mains plug connected to said therapy unit housing, so that power can be supplied from the existing mains system. In accordance with again an added feature of the invention, the connecting means are in the form of a battery.

In accordance with again a concomitant feature of the invention, there is provided a blower, such as a cooling fan, having means for infinitely graduating the speed of cold air supplied from said air outlet.

Through the use of the therapy unit constructed according to the invention, ambient air at various temperatures can be cooled down to a therapeutically useful below-zero ($-0°$ C.) temperature, with simple operation and low maintenance costs. The therapeutic need can be met by the correct selection of the interchangeable plug-in nozzle. It is also possible to add other gases or medical additives to the cold air to be applied, or to modify the cold air in some other way.

The unit according to the invention is advantageously usable above all in physical therapy, orthopedics, rheumatology, sports medicine, as well as in veterinary medicine.

Other features which are considered as characteristic for the invention are set forth in the appended claims.

Although the invention is illustrated and described herein as embodied in a cryotherapy unit, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

The drawing is a diagrammatic, perspective view of a therapy unit.

Referring now to the single FIGURE of the drawing in detail, it is seen that an integrated cooling system 4 is disposed in a therapy unit housing 1. Ambient air is supplied to the therapy unit housing 1 through an air inlet 2. After being cooled down, the air is carried to an application site on the patient through an air outlet 3 and an isolating hose 10 connected thereto. A blower or ventilator 16 such as a cooling fan is provided with means for infinitely graduating the speed of cold air from the air outlet. The free end of the isolating hose 10 is provided with one of several slip-on nozzles 9 which are constructed to suit applicable conditions.

A thermostat control system 7 and at least one thermometer 8, 8' are provided. The thermometer 8 is disposed on the front surface of the therapy unit housing 1 for measuring the temperature of the ambient air. Another thermometer 8' is disposed on the isolating hose 10 for measuring the temperature at an application site. An acoustic and/or optical signal transducer 14 is associated with the air outlet 3 for displaying a deviation of a set temperature for cold air flowing out of the air outlet.

Means are provided for connecting the cooling system to a mains system or current source for the supply of power. The connecting means may be a mains plug 5, a battery 13 or a combination thereof. For easier transportation of the therapy unit housing 1, wheels 6 are directly disposed on the underside or they may be disposed on a base 15 and therefore indirectly associated with the therapy unit housing 1.

According to another embodiment of the invention shown in phantom, the cooling system 4 is a split system, and a cooling unit 11, such as a compressor, as well as a condenser 12 of the cooling system are disposed outside the therapy unit housing 1 and connected thereto by lines 17. In this way, several therapy unit housings can be connected to one cooling system.

I claim:

1. Cryotherapy unit for cold application to a therapeutic application site by cooled ambient air, comprising a cooling system operable without the use of liquid nitrogen and including a refrigerating unit and a condenser, means for connecting said cooling system to a current source, a therapy unit housing into which said cooling system is integrated, an air inlet in communication with said cooling system, an air outlet in communication with said cooling system, a blower having means for graduating the speed of cold air supplied from said air outlet, and an insulated hose connected to said air outlet, for guiding cooled air to the therapeutic application site.

2. Therapy unit according to claim 1, including a slip-on nozzle interchangeably connected to said insulated hose.

3. Therapy unit according to claim 1, including a thermostat control system disposed on said therapy unit housing.

4. Therapy unit according to claim 1, including an acoustic signal transducer associated with said air outlet for displaying a deviation of a set temperature for cold air flowing out of said air outlet.

5. Therapy unit according to claim 1, including an optical signal transducer associated with said air outlet for displaying a deviation of a set temperature for cold air flowing out of said air outlet.

6. Therapy unit according to claim 1, including an acoustic and optical signal transducer associated with said air outlet for displaying a deviation of a set temperature for cold air flowing out of said air outlet.

7. Therapy unit according to claim 1, including at least one thermometer disposed on said therapy unit housing for measuring the temperature of the ambient air.

8. Therapy unit according to claim 1, including and at least one thermometer disposed on said insulated hose for measuring the temperature at the application site.

9. Therapy unit according to claim 1, including a thermometer disposed on said therapy unit housing for measuring the temperature of the ambient air and another thermometer disposed on said insulated hose for measuring the temperature at the application site.

10. Therapy unit according to claim 1, including wheels directly associated with said therapy unit housing for transportation.

11. Therapy unit according to claim 1, including wheels indirectly associated with said therapy unit housing for transportation.

12. Therapy unit according to claim 1, wherein said connecting means are in the form of a mains plug connected to said therapy unit housing.

13. Therapy unit according to claim 1, wherein said connecting means are in the form of a battery.

14. Therapy unit according to claim 1, wherein said graduating means are means for infinitely graduating the speed of cold air supplied from said air outlet.

15. Therapy unit according to claim 1, wherein said blower is a cooling fan.

* * * * *